United States Patent
Shinbata

(10) Patent No.: US 7,139,419 B2
(45) Date of Patent: Nov. 21, 2006

(54) IMAGE PROCESSING APPARATUS, METHOD AND STORAGE MEDIUM

(75) Inventor: Hiroyuki Shinbata, Tochigi-ken (JP)

(73) Assignee: Canon Kabushiki Kaisha, Tokyo (JP)

(*) Notice: Subject to any disclaimer, the term of this patent is extended or adjusted under 35 U.S.C. 154(b) by 317 days.

(21) Appl. No.: 10/857,855

(22) Filed: Jun. 2, 2004

(65) Prior Publication Data

US 2004/0223658 A1   Nov. 11, 2004

Related U.S. Application Data

(62) Division of application No. 09/526,540, filed on Mar. 16, 2000, now Pat. No. 6,904,181.

(30) Foreign Application Priority Data

Mar. 19, 1999   (JP)   ............... 11-076881

(51) Int. Cl.
  *G06K 9/00*   (2006.01)
  *G01N 23/04*   (2006.01)
  *G06K 9/20*   (2006.01)

(52) U.S. Cl. .................. 382/132; 382/282; 250/582

(58) Field of Classification Search ........... 382/132, 382/128, 131, 168, 171, 172, 282; 250/580, 250/581, 582, 584, 200, 206, 206.1, 206.2, 250/472.1, 473.1; 378/4, 9, 11, 12, 16, 19, 378/20
See application file for complete search history.

(56) References Cited

U.S. PATENT DOCUMENTS

| | | | |
|---|---|---|---|
| 4,859,850 A | 8/1989 | Funahashi et al. | 250/327.2 |
| 4,931,642 A * | 6/1990 | Hosoi et al. | 250/586 |
| 5,151,947 A | 9/1992 | Nagatsuka et al. | 382/6 |
| 5,235,510 A * | 8/1993 | Yamada et al. | 600/300 |
| 5,588,071 A | 12/1996 | Schultz | 382/168 |
| 5,644,649 A | 7/1997 | Schoeters et al. | 382/132 |
| 5,883,972 A | 3/1999 | Ito | 382/132 |
| 5,954,796 A | 9/1999 | Mcarty et al. | 709/222 |
| 6,314,198 B1 | 11/2001 | Ogura | 382/132 |

FOREIGN PATENT DOCUMENTS

| | | |
|---|---|---|
| EP | 0964362 A1 | 12/1999 |
| JP | 2000-70243 | 8/1998 |
| JP | 10-243020 | 9/1998 |

* cited by examiner

*Primary Examiner*—Yon J. Couso
(74) *Attorney, Agent, or Firm*—Fitzpatrick, Cella, Harper & Scinto

(57) ABSTRACT

An image processing apparatus which can always accurately extract, from a photographed image, an optimum feature quantity to be used for image processing is provided. In the apparatus, a limitation unit limits a predetermined area to extract the feature quantity in a lung area of an image (lung image obtained by radiographing). For example, as the predetermined area, the limitation unit limits an area obtained by dividing the lung area in a predetermined ratio, an area extending from ¼ to ½ from a head side of a maximum-length vertical axis of the lung area, or an area within a predetermined-length range from the upside of the lung area. An extraction unit extracts a feature quantity (maximum pixel value) from the predetermined area.

9 Claims, 9 Drawing Sheets

IMAGE PROCESSING APPARATUS, METHOD AND STORAGE MEDIUM

CROSS REFERENCE TO RELATED APPLICATION

This application is a division of application Ser. No. 09/526,540, filed Mar. 16, 2000 now U.S. Pat. No. 6,904,181.

BACKGROUND OF THE INVENTION

1. Field of the Invention

The present invention relates to image processing apparatus, system and method which are used in an apparatus and a system for extracting a feature quantity from an image obtained by radiographing (e.g., X-ray photographing), and performing gradation conversion processing for the photographed image on the basis of the feature quantity. The present invention also relates to a storage medium which computer-readably stores a program of processing steps to execute the above image processing method.

2. Related Background Art

In recent years, by the advancement of a digital technology, for example, an image photographed by X-ray photographing is digitized, the obtained digital image is subjected to image processing, and the processed image is displayed on a monitor or output onto an X-ray diagnosis film.

As the above image processing, there is gradation conversion processing which converts the photographed image to have a density value easy to be observed on an output destination such as a monitor screen, the film or the like.

In the gradation conversion processing, for example, when an image photographed by X-ray photographing a lung area is output onto the X-ray diagnosis film, a histogram of all pixels constituting the photographed image is first formed, and the formed histogram is analyzed. Next, a pixel value at a point of a certain part (e.g., an upper 5% point) of the histogram is extracted as a feature quantity of the photographed image. Then conversion of a density value (i.e. gradation conversion) is performed such that the extracted pixel value (the feature quantity) becomes a certain density value (a density of 1.9 or so) on the film.

However, in such a conventional image processing method as described above, especially the following problems are enumerated.

First, to perform the image processing to the photographed image of the lung area, conventionally the value of the point of the certain part (e.g., the upper 5% point) is extracted as the feature quantity from the histogram of the entire photographed image. This feature quantity is always extracted from the point of the certain part such as the upper 5% point or the like, irrespective of a state of a subject (e.g., a constitution of the subject) on the photographed image. Thus, even if the gradation conversion is performed based on such the feature quantity, a density distribution of the image after converting the gradation might vary according to the kind of the photographed target image. Therefore, when diagnosis is performed by using such the image which is obtained after converting the gradation and of which density distribution varies, there is some fear that a diagnosis mistake is invited. This is the serious problem.

Further, a necessary area and an unnecessary area (a transparent area or a transmission area) exist in the image photographed by the X-ray photographing. In the necessary area, the X-ray which permeated a subject hits a sensor surface, while in the unnecessary area, the X-ray directly and strongly hits the sensor surface. Incidentally, the feature quantity used for the image processing is conventionally extracted from the histogram of the entire photographed image. Namely, the feature quantity used for the image processing is extracted from information of the entire photographed image including information of the unnecessary area (the transparent area). Therefore, a desired feature quantity can not be extracted, whereby the image which is obtained after converting the gradation and is optimum for observation can not be obtained. This is also the serious problem.

SUMMARY OF THE INVENTION

The present invention is made to solve the above-described problems, and an object thereof is to provide an image processing apparatus, an image processing system, an image processing method, and a storage medium computer-readably storing a program composed of processing steps to perform the above image processing method. Concretely, the object is to be able to accurately extract at any time an optimum feature quantity used for image processing from a photographed image, whereby it is possible to perform optimum image processing and output a satisfactory image.

Under such the object, a first invention is featured by a structure that a limitation means for limiting a predetermined area on an image, an extraction means for extracting a feature quantity from the predetermined area limited by the limitation means, and a setting means for setting an image processing parameter on the basis of the feature quantity obtained by the extraction means are provided.

Another invention is featured by a structure that, in the first invention, the image includes an image obtained by photographing an arbitrary subject, and the limitation means limits a predetermined area within a subject area existing on the image.

Still another invention is featured by a structure that a lung area in an image obtained by photographing a lung as a subject is divided in a predetermined ratio, and the divided area is limited as a predetermined area.

Still another invention is featured by a structure that a feature quantity is extracted from an area extending from ¼ to ½ from a head side of a maximum-length vertical axis of an lung area.

Other objects and features of the present invention will become apparent from the following detailed description and the attached drawings.

DETAILED DESCRIPTION OF THE PREFERRED EMBODIMENTS

Hereinafter, the preferred embodiments of the present invention will be explained with reference to the attached drawings.

(First Embodiment)

Figure 1:
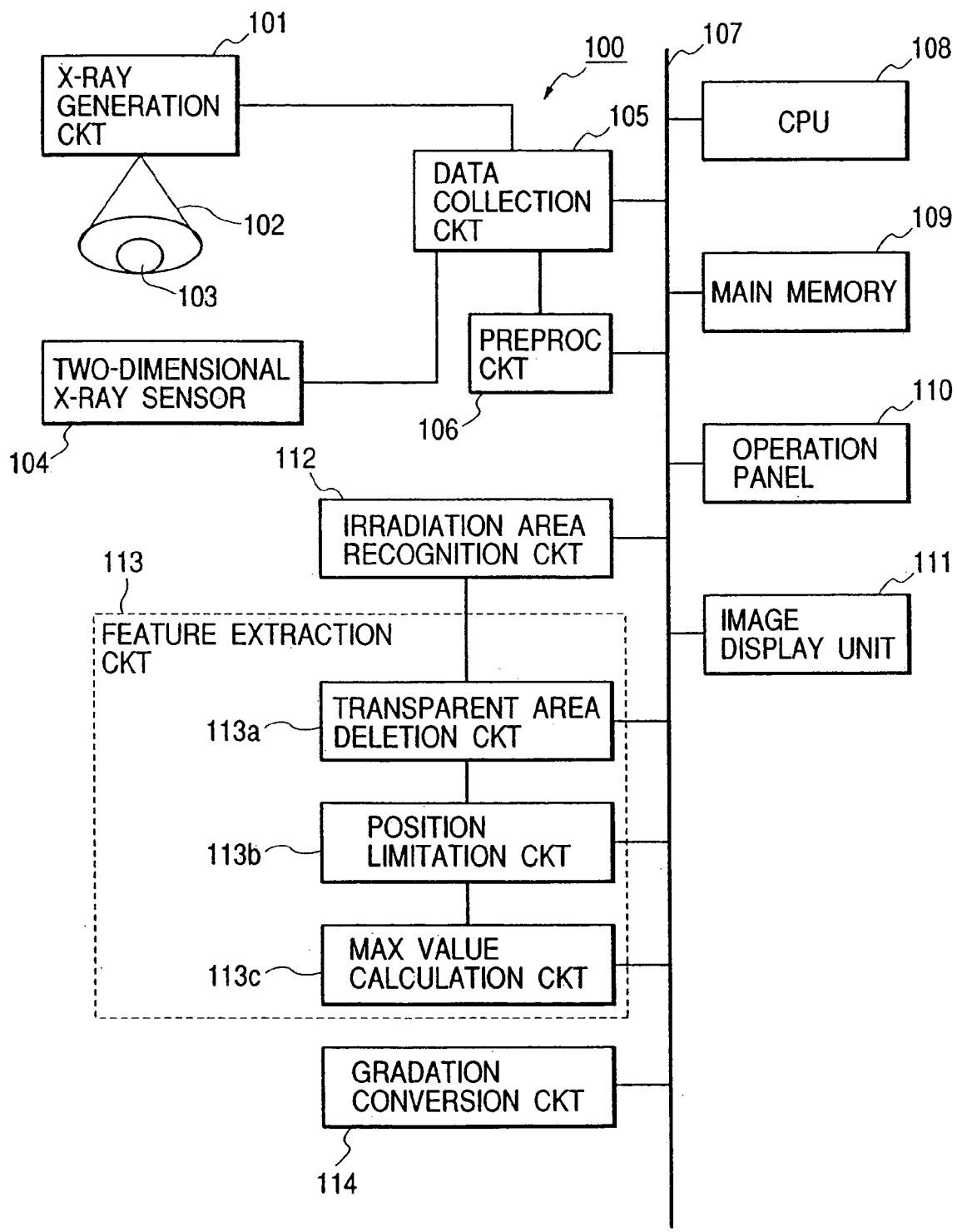
FIG. 1 is a block diagram showing a structure of an X-ray photographing apparatus according to the first embodiment of the present invention.

The present embodiment is applied to, e.g., such an X-ray photographing apparatus 100 as shown in FIG. 1.

The X-ray photographing apparatus 100 has an image processing function for a photographed image. As shown in FIG. 1, the X-ray photographing apparatus 100 includes an X-ray generation circuit 101 which generates an X-ray beam 102, a two-dimensional X-ray sensor 104 on which the X-ray beam 102 penetrated through a subject 103 is imaged, a data collection circuit 105 which collects photographed images output from the two-dimensional X-ray sensor 104, a preprocessing circuit 106 which performs preprocessing to the photographed images collected by the data collection circuit 105, a main memory 109 which stores various information such as the photographed image (original image) subjected to the preprocessing by the preprocessing circuit 106 and processing programs to perform various processing, an operation panel 110 which is used to instruct X-ray photographing and perform various setting to the X-ray photographing apparatus 100, an irradiation area recognition circuit 112 which extracts an irradiation area from the photographed image (original image) subjected to the preprocessing by the preprocessing circuit 106, a feature extraction circuit 113 which extracts a feature quantity from the image of the irradiation area obtained by the irradiation area recognition circuit 112, a gradation conversion circuit 114 which performs with use of the feature quantity obtained by the feature extraction circuit 113 gradation conversion processing to the photographed image (original image) subjected to the preprocessing by the preprocessing circuit 106, an image display unit 111 which displays the photographed image subjected to the gradation conversion processing by the gradation conversion circuit 114, and a CPU 108 which controls an operation of the X-ray photographing apparatus 100 as a whole. The data collection circuit 105, the preprocessing circuit 106, the irradiation area recognition circuit 112, the feature extraction circuit 113, the gradation conversion circuit 114, the CPU 108, the main memory 109, the operation panel 110 and the image display unit 111 are all connected to a CPU bus 107 such that data can be transferred and received among these units.

The feature extraction circuit 113 which is structured to extract the feature quantity from a predetermined area limited in the photographed image is the most important feature in the present embodiment. Thus, even if the photographed image subjected to the gradation conversion processing by the gradation conversion circuit 114 is what one, a density value of the image after the gradation conversion can be kept constant.

Thus, the feature extraction circuit 113 includes a transparent area deletion circuit 113a which deletes a transparent area (i.e., an area where X-ray does not penetrate a subject) and a certain area adjacent to the transparent area from the photographed image, a position limitation circuit 113b which calculates (i.e., limits) a predetermined area from an area not deleted by the transparent area deletion circuit 113a, and a maximum value calculation circuit 113c which calculates a maximum pixel value from the area calculated by the position limitation circuit 113b. Therefore, the gradation conversion circuit 114 which is disposed at the later stage of the feature extraction circuit 113 performs the gradation conversion to the photographed image with use of the maximum pixel value as the feature quantity.

Figure 2:
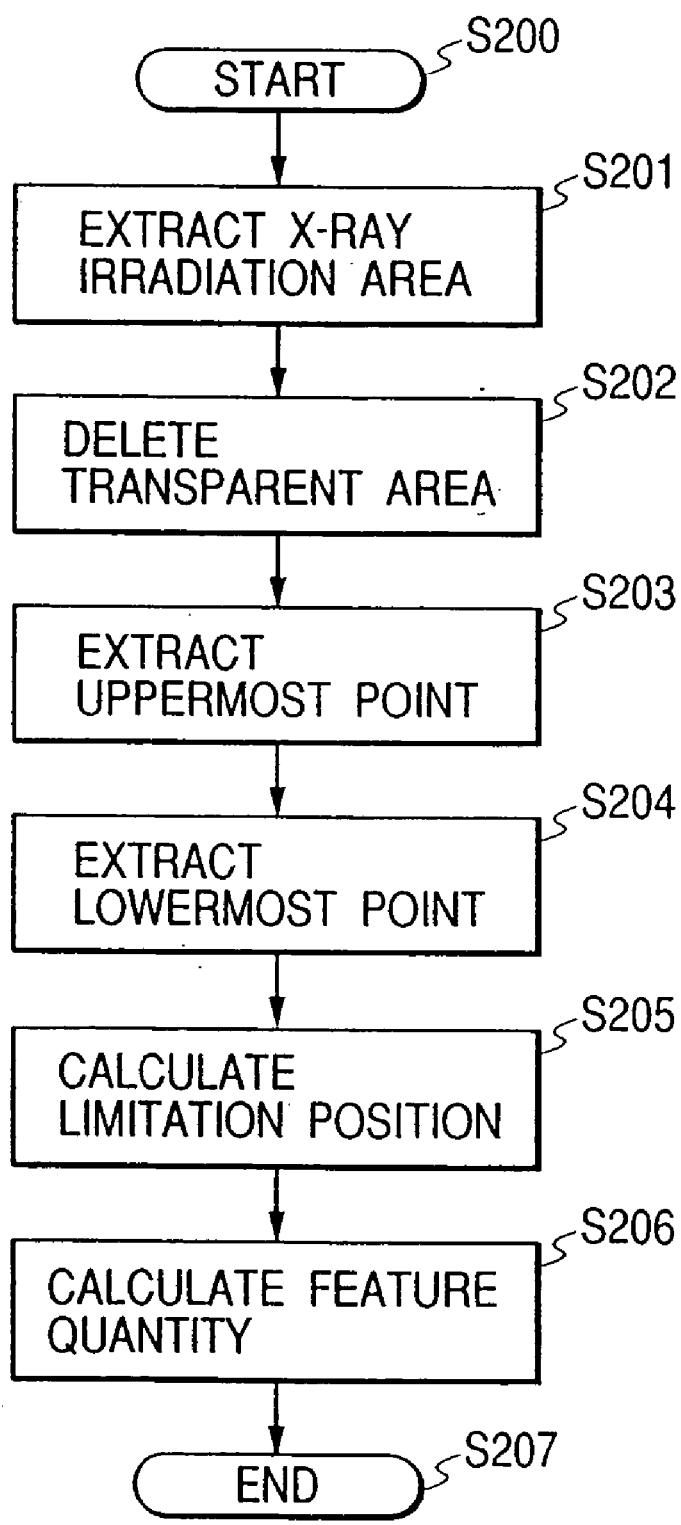
FIG. 2 is a flow chart for explaining an operation of the X-ray photographing apparatus.

In such the X-ray photographing apparatus 100 as above, initially data which is necessary for performing various processing by the CPU 108, processing programs and the like are previously stored in the main memory 109. Besides, the main memory 109 includes a working memory for the CPU 108. As the processing program (especially for extracting the feature quantity) which is previously stored in the main memory 109, for example, a processing program according to a flow chart shown in FIG. 2 is used.

Therefore, the CPU 108 reads the processing program from the main memory 109 and executes the read program, thereby controlling the entire operation of the X-ray photographing apparatus according to instructions from the operation panel 110, as explained below.

In a step S200, the X-ray generation circuit 101 generates the X-ray beam 102 to the subject (i.e., a body to be examined) 103. The X-ray beam 102 generated by the X-ray generation circuit 101 penetrates the subject 103 while attenuating. Then the X-ray beam 102 reaches the two-dimensional X-ray sensor 104, and is output therefrom as an X-ray image.

Figure 3:
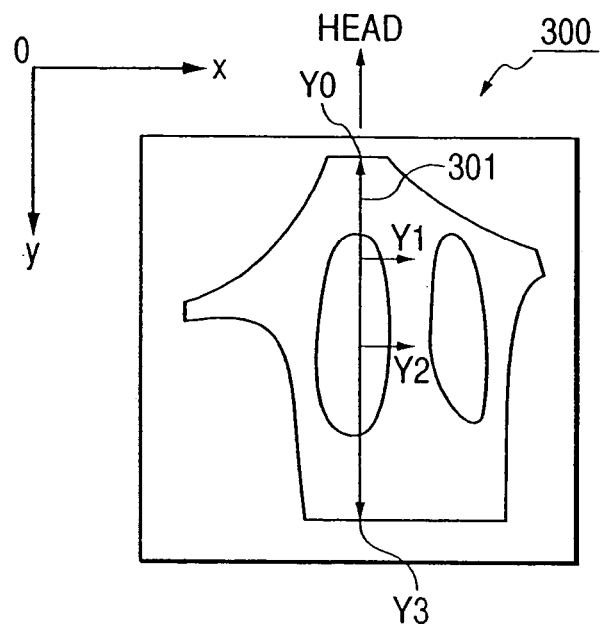
FIG. 3 is a view for explaining an example of a photographed image which is subjected to processing by the X-ray photographing apparatus.

In the present embodiment, it is assumed that the X-ray image output from the two-dimensional X-ray sensor 104 is, e.g., a lung front image 300. FIG. 3 shows the image in a state that a transparent area (i.e., an area where X-ray directly hits a sensor) and a certain-width area adjacent to the transparent area were deleted by the later-described transparent area deletion circuit 113a. In FIG. 3, numeral 301 denotes a maximum-length vertical axis line of the image after deletion of the transparent area, symbol Y1 denotes a position of ¼ from the head side on the maximum-length vertical axis line, and symbol Y2 denotes a position of ½ from the head side on the maximum-length vertical axis line.

Next, the data collection circuit 105 converts the X-ray image output from the two-dimensional X-ray sensor 104 into an electrical signal, and supplies the obtained signal to the preprocessing circuit 106.

The preprocessing circuit 106 performs the preprocessing such as offset correction processing, gain correction processing and the like to the signal (X-ray image signal) supplied from the data collection circuit 105. Under the control of the CPU 108, the X-ray image signal subjected to the preprocessing by the preprocessing circuit 106 is transferred as input image information to the main memory 109, the irradiation area recognition circuit 112, the feature extraction circuit 113 and the gradation conversion circuit 114, through the CPU bus 107.

In a step S201, the irradiation area recognition circuit 112 analyzes an input image (also called a target image hereinafter) transferred under the control of the CPU 108, with use of an arbitrary method (e.g., the method disclosed in U.S. patent application Ser. No. 09/287,406 filed on Apr. 6, 1999: corresponding to Japanese Patent Application No. 10-243020), thereby extracting an X-ray irradiation area.

On the basis of the irradiation area extracted by the irradiation area recognition circuit 112, the feature extraction circuit 113 performs processing in later-described steps S202, S203, S204, S205 and S206, to the input image (target image) transferred under the control of the CPU 108.

In the step S202, the transparent area deletion circuit 113a first replaces the outside of the irradiation area, the transparent area and the body area adjacent to the transparent area in a certain interval by, e.g., the pixel value="0".

Concretely, the image is converted as input image data f(x, y) by using a following expression (1), thereby obtaining image data f1 (x, y) from which the outside of the irradiation area, the transparent area and the body area adjacent to the transparent area in the certain interval were deleted.

$$f1(x, y) = f(x, y) \times \prod_{x1=-d1}^{x1=d1} \prod_{y1=-d2}^{y1=d2} sgn(x + x1, y + y1) \qquad (1)$$

Here, sgn(x, y) in the expression (1) is represented by using an expression (2).

$$sgn(x, y)=0 \text{ when } f(x, y)>Th1 sgn(x, y)=1 \text{ when other cases} \qquad (2)$$

In the expression (2), the constant Th1 is previously obtained by an experiment or the like. For example, it is assumed that the constant Th1 is 5% of the maximum value of the pixel value of the input image (original image). Further, the constants d1 and d2 in the expression (1) are used to determine the certain interval (certain width) of body area adjacent to the transparent area.

The input image (i.e., the image f1 (x, y)) obtained after the processing of the transparent area deletion circuit 113a is the image 300 shown in FIG. 3.

Next, in the steps S203 and S204, the position limitation circuit 113b extracts the area of which pixel value is not "0", i.e., uppermost and lowermost points Y0 and Y3 of the subject area on the maximum-length vertical axis line 301 (see FIG. 3) of the image f1 (x, y) obtained by the transparent area deletion circuit 113a.

Next, in the step S205, the position limitation circuit 113b calculates the position Y1 of ¼ from the uppermost point Y0 on the maximum-length vertical axis line 301 by using a following expression (3), on the basis of the uppermost and lowermost points Y0 and Y3 extracted in the steps S203 and S204.

$$Y1=Y0+(Y3-Y0)/4 \qquad (3)$$

Further, the position limitation circuit 113b calculates the position Y2 of ½ from the uppermost point Y0 on the maximum-length vertical axis line 301 by using a following expression (4), on the basis of the uppermost and lowermost points Y0 and Y3 extracted in the steps S203 and S204.

$$Y2=Y0+(Y3-Y0)/2 \qquad (4)$$

Thus, the position limitation circuit 113b sets the image area of which pixel value is not "0" (i.e., image f1 (x, y)>0) but satisfies $Y1<y \leq Y2$, as a limitation area.

In the step S206, the maximum value calculation circuit 113c calculates a maximum pixel value max within the limitation area obtained by the position limitation circuit 113b, by using a following expression (5).

$$\max=\max\{f1(x, y)|Y1 \leq y \leq Y2\} \qquad (5)$$

The obtained result max is the feature quantity which is used in the gradation conversion processing performed in a next step S207.

It should be noted that the method to calculate the maximum value max in the step S206 is not limited to that of the expression (5). For example, in the limitation area which satisfies that the image f1 (x, y)>0 and $Y1 \leq y \leq Y2$, it is possible to sort the pixel value from the large one and set the value at the upper 5% point as the maximum value max. Otherwise, it is possible to set the average of the pixel values up to the upper 5% point as the maximum value max.

Figure 4:
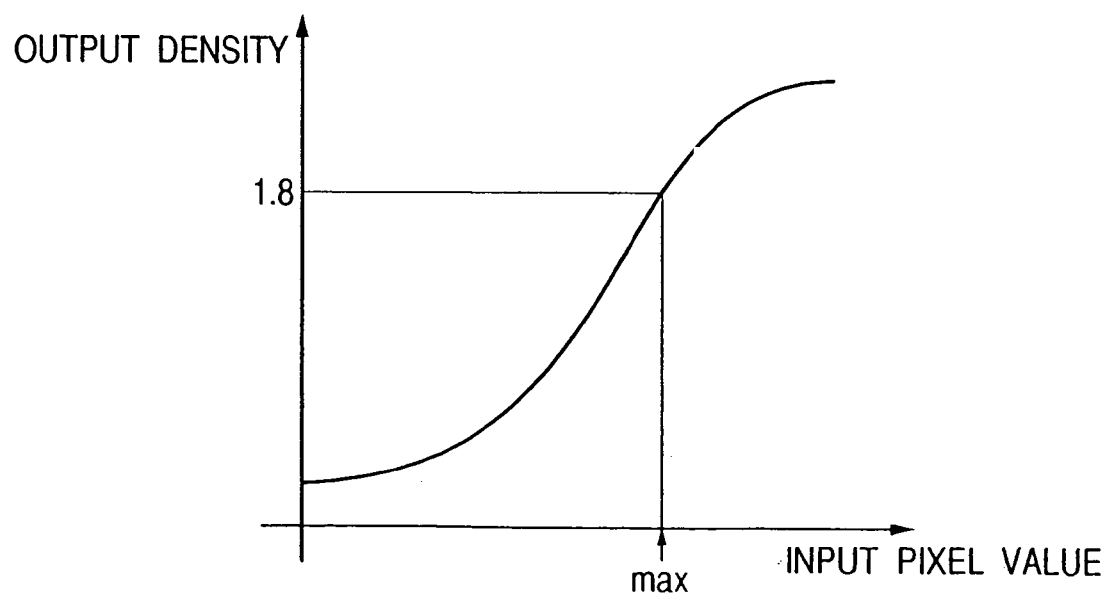
FIG. 4 is a view for explaining a gradation conversion curve in gradation conversion processing by the X-ray photographing apparatus.

In the step S207, the gradation conversion circuit 114 performs the gradation conversion to the input image transferred under the control of the CPU 108 such that the maximum value max (feature quantity) calculated by the maximum value calculation circuit 113c has the output density of, e.g., 1.8, as shown in FIG. 4. The image subjected to the gradation conversion processing by the gradation conversion circuit 114 is displayed on the image display unit 111 or output on a film.

As described above, according to the present embodiment, it is structured that, in the photographed image, the area from which the feature quantity is extracted is limited to the predetermined area of the subject. For the photographed image obtained by photographing the subject in any state, it is possible to extract the feature quantity corresponding to such the photographed image. Besides, even if the subject is what constitution, it is possible to extract the feature quantity corresponding to such the constitution. Thus, it is possible to keep constant the density value of the predetermined area of the subject in the image after the gradation conversion. Therefore, it is possible to satisfactorily observe the photographed image on the monitor screen, the film and the like, thereby improving diagnosis ability or the like.

Further, for example, when a lung is photographed, the areas of which pixel values are extremely high exist at the upper and lower parts of the lung area in the photographed image. Thus, if the pixel value of such the part is extracted as the feature quantity, there is some fear that the density value of the predetermined area in the image after the gradation conversion deviates from the predetermined value. However, in the present embodiment, it is possible not to include the upper and lower parts of the lung area in the limitation area, and such an operation is especially effective for the image obtained by photographing the lung.

Further, when the feature quantity is extracted from the limitation area, if it is structured that the pixel values of certain ratio from the highest pixel value are extracted from the pixel values in this limitation area, it is possible to extract the optimum feature quantity without being influenced by a noise and the like, thereby obtaining a more-stable image after the gradation conversion.

Further, for example, when the image after the gradation conversion is output to the film and the density value of the predetermined area of the output image is measured by a densitometer, if it is structured that the average of the pixels up to the upper 5% point pixels in the limitation area is set as the feature quantity, the average density of the pixel values in the area substantially equal to a measurement area point of the densitometer is extracted as the feature quantity used for the gradation conversion. Thus, it is possible to make the density value of the predetermined area of the image after the gradation conversion equal to the density value actually measured by the densitometer.

Further, when the size of the subject to be photographed does not greatly differ, since the lung is positioned in the substantially same area of the photographed image, the limitation area is determined from the length in the vertical direction of the original image. By such a structure, it is possible to determine the limitation area which is suitable to extract the feature quantity not including the upper and lower edge areas of the lung, in stability and a short time.

In the above first embodiment, for example, it is possible to perform the processing by using a following expression (6) to the image f1 (x, y) (i.e., the image after the processing of the transparent area deletion circuit 113a: see the step S202) to calculate an image f2 (x, y). Then by using the calculated image f2 (x, y), it is possible to perform the processing beginning from the step S203.

$$f2(x, y)=f1(x, y) \text{ when } f1(x, y) \leq Th2 sgn(x, y)=0 \text{ when other cases} \quad (6)$$

In this case, the maximum value calculation circuit 113c calculates the maximum pixel value max by using a following expression (7) instead of the expression (5).

$$\max=\max(f2(x, y)|Y1 \leq y \leq Y2) \quad (7)$$

Here, it is assumed in the expression (6) that the constant Th2 is, e.g., the pixel value of 80% of the maximum pixel value in the lung area of the photographed image.

Concretely, for example, in the image f1 (x, y) after the transparent area deletion, the area not converted into "0" by the expressions (1) and (2) is extracted as the lung area, and the pixel value of 80% of the maximum pixel value in the extracted lung area is set as the constant Th2. Then the processing based on the expression (6) is further performed. Thus, the limitation area obtained by the position limitation circuit 113b becomes the area substantially extending from (or between) ¼ to ½ from the head side of the lung area. The pixels equal to or lower than the constant Th2 correspond to an abdomen area and a mediastinum area, because the substantial lung area can be extracted under the condition of the expression (6).

Further, in the above first embodiment, the position Y1 of ¼ and the position Y2 of ½ from the uppermost point Y0 on the maximum-length vertical axis line 301 are calculated by using the expressions (3) and (4) respectively. However, for example, it is fixedly set the positions Y1 and Y2 from the uppermost point Y0 to be respectively 5 cm and 15 cm, 10 cm and 20 cm, and the like (i.e., to have fixed values previously obtained according to the size of two-dimensional X-ray sensor). Thus, for example, in the lung-photographed image obtained on the premise that the sizes of adult lungs are substantially the same, it is possible to easily eliminate the upper and lower parts of the lung of which X-ray transmittance is high.

Further, in the above first embodiment, the uppermost and lowermost points Y0 and Y3 of the area where the pixel value is not "0" are extracted (see the steps S203 and S204). However, for example, it is possible to extract the uppermost and lowermost points of the original image (input image) itself as the points Y0 and Y3, because of the following reason. Namely, when the size of the subject does not greatly differ in the standing photographing of the lung, the lung area is positioned in the substantially same area on the original image. Thus, even if the limitation area is determined from the length in the vertical direction of the original image, such the limitation area does not include the upper and lower edge areas of the lung.

(Second Embodiment)

Figure 5:
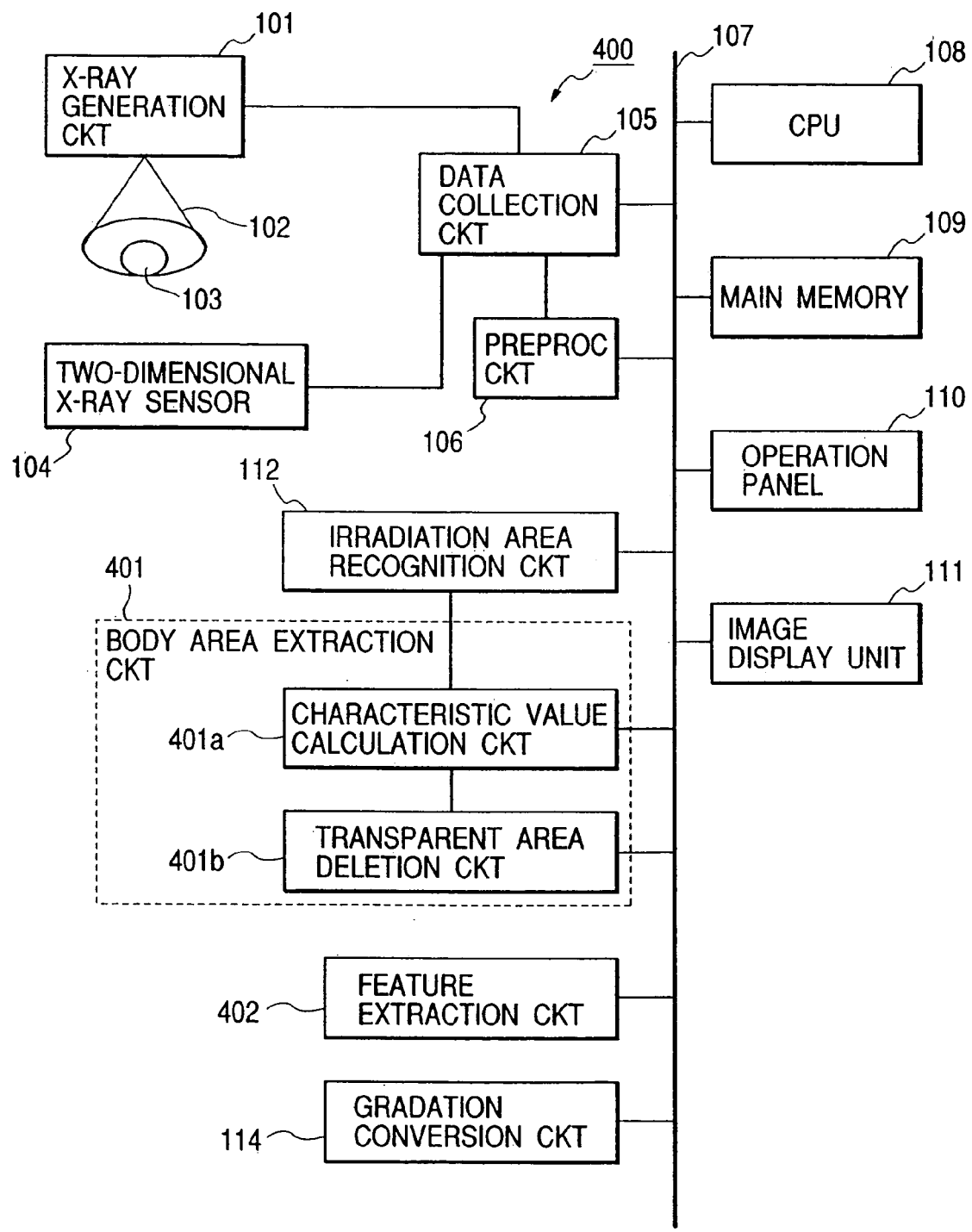
FIG. 5 is a block diagram showing a structure of an X-ray photographing apparatus according to the second embodiment of the present invention.

The present embodiment is applied to, e.g., such an X-ray photographing apparatus 400 as shown in FIG. 5.

The X-ray photographing apparatus 400 has an image processing function for a photographed image. As shown in FIG. 5, the X-ray photographing apparatus 400 includes an X-ray generation circuit 101 which generates an X-ray beam 102, a two-dimensional X-ray sensor 104 on which the X-ray beam 102 penetrated through a subject 103 is imaged, a data collection circuit 105 which collects photographed images output from the two-dimensional X-ray sensor 104, a preprocessing circuit 106 which performs preprocessing to the photographed images collected by the data collection circuit 105, a main memory 109 which stores various information such as the photographed image (original image) subjected to the preprocessing by the preprocessing circuit 106 and processing programs to perform various processing, an operation panel 110 which is used to instruct X-ray photographing and perform various setting to the X-ray photographing apparatus 400, an irradiation area recognition circuit 112 which extracts an irradiation area from the photographed image (original image) subjected to the preprocessing by the preprocessing circuit 106, a body area extraction circuit 401 which extracts an area where a later-described feature quantity is extracted from the image of the irradiation area obtained by the irradiation area recognition circuit 112, a feature extraction circuit 402 which extracts the feature quantity from the area obtained by the body area extraction circuit 401, a gradation conversion circuit 114 which performs with use of the feature quantity obtained by the feature extraction circuit 402 gradation conversion processing to the photographed image (original image) subjected to the preprocessing by the preprocessing circuit 106, an image display unit 111 which displays the photographed image subjected to the gradation conversion processing by the gradation conversion circuit 114, and a CPU 108 which controls an operation of the X-ray photographing apparatus 400 as a whole. The data collection circuit 105, the preprocessing circuit 106, the irradiation area recognition circuit 112, the body area extraction circuit 401, the feature extraction circuit 402, the gradation conversion circuit 114, the CPU 108, the main memory 109, the operation panel 110 and the image display unit 111 are all connected to a CPU bus 107 such that data can be transferred and received among these units.

The body area extraction circuit 401 which is structured to calculate a characteristic value used to determine an unnecessary area (e.g., a transparent area where an X-ray directly hits a sensor) of the photographed image and delete the unnecessary area from the photographed image on the basis of the calculated characteristic value is the most important feature in the present embodiment.

Thus, the body area extraction circuit 401 includes a characteristic value calculation circuit 401a which calculates the characteristic value to determine the unnecessary area in the photographed image, and a transparent area deletion circuit 401b which deletes the unnecessary area from the photographed image on the basis of the characteristic value calculated by the characteristic value calculation circuit 401a.

Therefore, the feature extraction circuit 402 extracts the feature quantity used for the gradation conversion processing by the gradation conversion circuit 114, from the area from which the unnecessary area was deleted by the body area extraction circuit 401, i.e., information based on only a necessary area (body area).

Figure 6:
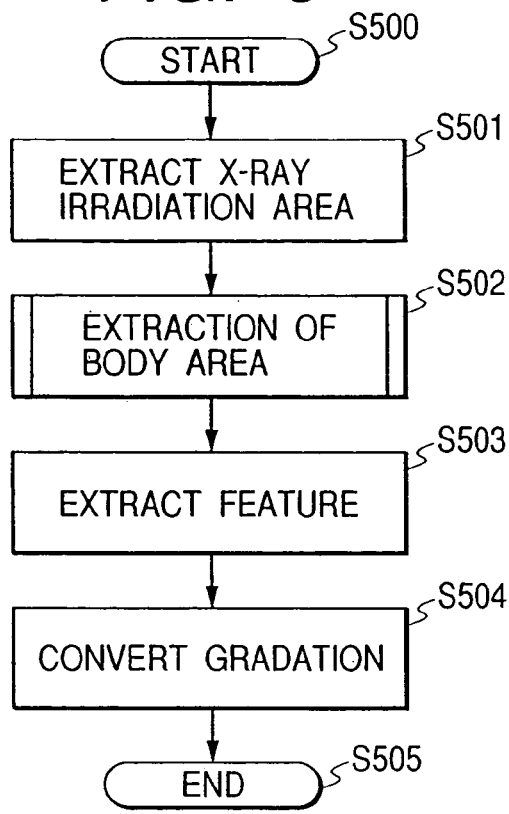
FIG. 6 is a flow chart for explaining an entire operation of the X-ray photographing apparatus.
Figure 7:
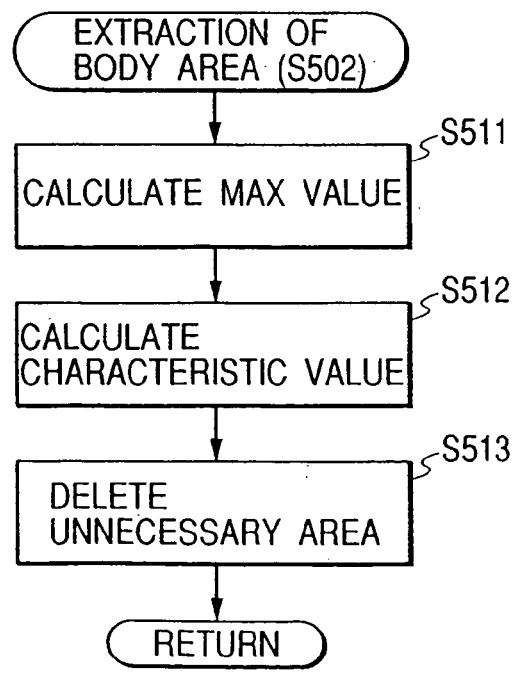
FIG. 7 is a flow chart for explaining a body area extraction processing in the flow chart of FIG. 6.

In such the X-ray photographing apparatus 400 as above, initially data which is necessary for performing various processing by the CPU 108, processing programs and the like are previously stored in the main memory 109. Besides, the main memory 109 includes a working memory for the CPU 108. As the processing program which is previously stored in the main memory 109, for example, a processing program according to flow charts shown in FIGS. 6 and 7 is used.

Therefore, the CPU 108 reads the processing program from the main memory 109 and executes the read program, thereby controlling the entire operation of the X-ray photographing apparatus 400 according to instructions from the operation panel 110, as explained below.

In the X-ray photographing apparatus 400 of FIG. 5, the parts which function as well as the parts in the X-ray photographing apparatus 100 of FIG. 1 are added with the same reference numerals as those in FIG. 1 respectively, and detailed explanation thereof will be omitted.

In a step S500, the X-ray generation circuit 101 generates the X-ray beam 102 to the subject (i.e., a body to be examined) 103. The X-ray beam 102 generated by the X-ray generation circuit 101 penetrates the subject 103 while attenuating, and reaches the two-dimensional X-ray sensor 104. Then the X-ray beam 102 is output as an X-ray image by the X-ray sensor 104. In the present embodiment, it is assumed that the X-ray image output from the X-ray sensor 104 is a human body image.

Next, the data collection circuit 105 converts the X-ray image output from the two-dimensional X-ray sensor 104 into an electrical signal, and supplies the obtained signal to the preprocessing circuit 106.

The preprocessing circuit 106 performs the preprocessing such as offset correction processing, gain correction processing and the like to the signal (X-ray image signal) supplied from the data collection circuit 105. Under the control of the CPU 108, the X-ray image signal subjected to the preprocessing by the preprocessing circuit 106 is transferred as input image information to the main memory 109, the irradiation area recognition circuit 112, the body area extraction circuit 401, the feature extraction circuit 402 and the gradation conversion circuit 114, through the CPU bus 107.

In a step S501, the irradiation area recognition circuit 112 extracts an X-ray irradiation area from an input image (also called a target image hereinafter) transferred under the control of the CPU 108, with use of an arbitrary method.

In a step S502, the body area extraction circuit 401 performs processing in later-described steps S511, S512 and S513 (see FIG. 7) on the basis of the irradiation area extracted by the irradiation area recognition circuit 112, thereby extracting a necessary area from the input image (target image) transferred under the control of the CPU 108.

First, in the step S511, the characteristic value calculation circuit 401a calculates a maximum value max of pixels in the input image. Concretely, for example, the characteristic value calculation circuit 401a forms a cumulative histogram of the entire input image, and sets a predetermined point (e.g., the upper 5% point) as the maximum value max. The purpose of this operation is to prevent influence of noise.

The method of calculating the maximum value max in the step S511 is not limited to such a method as above. Namely, an arbitrary method may be used. For example, it is possible to use a method of sorting all pixel values and then setting the predetermined point (e.g., the upper 5% point) as the maximum value max.

Next, in the step S512, the characteristic value calculation circuit 401a calculates a characteristic value Th from the maximum value max calculated in the step S511. Concretely, the characteristic value Th is calculated based on a constant C1 (e.g., 0.9), by using an expression (8).

$$Th = max \times C1 \quad (8)$$

Next, in the step S513, the transparent area deletion circuit 401b replaces pixels outside the irradiation area, pixels having value equal to or larger than the characteristic value Th, and pixels within the area adjacent in a certain interval to the pixels having the value equal to or larger than the value Th by, e.g., the pixel value="0" in the input image.

Concretely, the image is converted as input image data f(x, y) by using a following expression (9), thereby obtaining image data f1 (x, y).

$$f1(x, y) = f(x, y) \times \prod_{x1=-d1}^{x1=d1} \prod_{y1=-d2}^{y1=d2} \text{sgn}(x+x1, y+y1) \quad (9)$$

Here, sgn(x, y) in the expression (9) is represented by using an expression (10).

$$\text{sgn}(x, y) = 0 \text{ when } f(x, y) \geq Th \text{ } \text{sgn}(x, y) = 1 \text{ when other cases} \quad (10)$$

In the expression (9), the constants d1 and d2 represent distances from the pixel having the value equal to or larger than the characteristic value Th in the horizontal and vertical directions, respectively. Therefore, the pixels positioned within the horizontal and vertical distances d1 and d2 from the pixel having the value equal to or larger then the value Th are replaced by "0".

Figure 8:
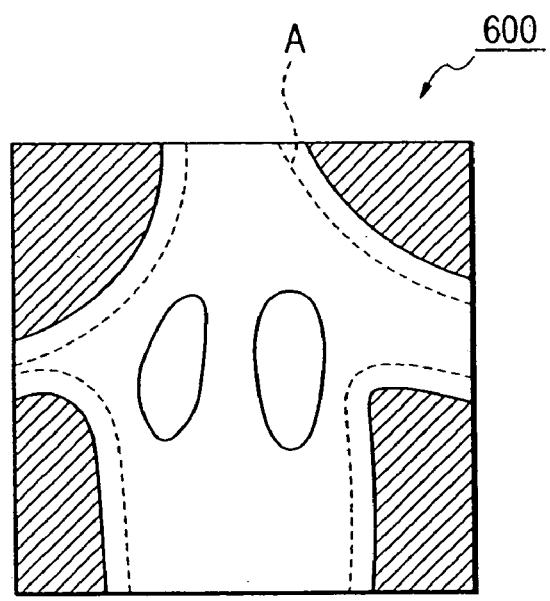
FIG. 8 is a view for explaining an example of photographed image which is subjected to processing by the X-ray photographing apparatus.

As a result, for example, the input image is converted into an image 600 as shown in FIG. 8. Namely, in the body area (i.e., a blank part) of the irradiation area, the pixels of the areas outside boundaries indicated by dotted lines A, i.e., outside the area (a soft tissue part) where an X-ray penetration quantity is large are replaced by "0".

Incidentally, when the processing based on the expression (8) is actually applied to the human body image, the pixels within the transparent area (the area where the X-ray directly hits a sensor) and the area adjacent to the transparent area in the distances d1 and d2 are replaced by "0".

In a step S503, when the above processing in the steps S511 to S513 is performed by the body area extraction circuit 401, the image f1 (x, y) obtained by deleting the unnecessary area from the photographed image, i.e., the image f1 (x, y) including only the necessary area can be given. Such the image f1 (x, y) is supplied to the feature extraction circuit 402.

The feature extraction circuit 402 extracts a feature quantity S1 used for the gradation conversion processing by the gradation conversion circuit 114, from the pixel area not having the pixel value "0" in the image f1 (x, y) obtained by the transparent area deletion circuit 401b.

Incidentally, the processing performed by the feature extraction circuit 113 in the first embodiment is applicable as the processing to be performed by the feature extraction circuit 402 in the present embodiment.

Figure 9:
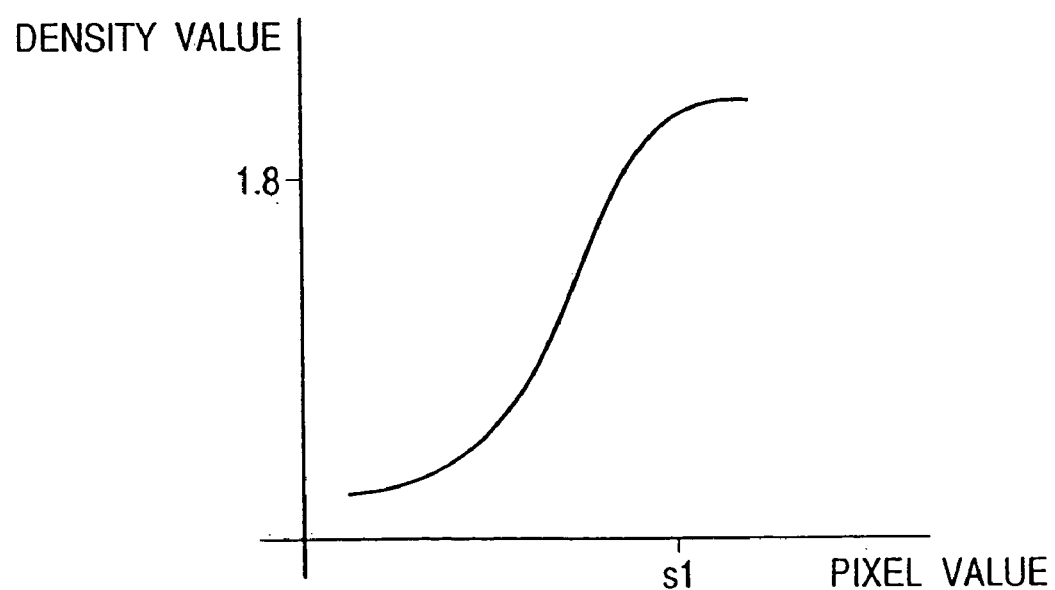
FIG. 9 is a view for explaining a gradation conversion curve in gradation conversion processing by the X-ray photographing apparatus.

In a step S504, as shown in FIG. 9, the gradation conversion circuit 114 performs the gradation conversion to the input image transferred under the control of the CPU 108, such that the feature quantity S1 calculated by the feature extraction circuit 402 has a density of, e.g., 1.8. The image subjected to the gradation conversion processing by the gradation conversion circuit 114 is displayed on the display unit 111 or output on a film.

As described above, according to the present embodiment, both the area (such as the transparent area where the X-ray directly hits the sensor) having the pixel value equal to or larger than the certain value and the certain-width area adjacent to the above area are certainly deleted by using the characteristic value obtained from the pixel value in the photographed image. Thus, it is possible to extract the feature quantity used for the gradation conversion processing, from only the information representing the necessary area such as the body area or the like.

Besides, according to the present embodiment, the characteristic value is determined from the maximum pixel value in the photographed image, whereby complicated analysis processing is unnecessary. Thus, it is possible to effectively and stably obtain the characteristic value in a short processing time, whereby it is possible to effectively perform the stable gradation conversion processing.

(Third Embodiment)

Figure 10:
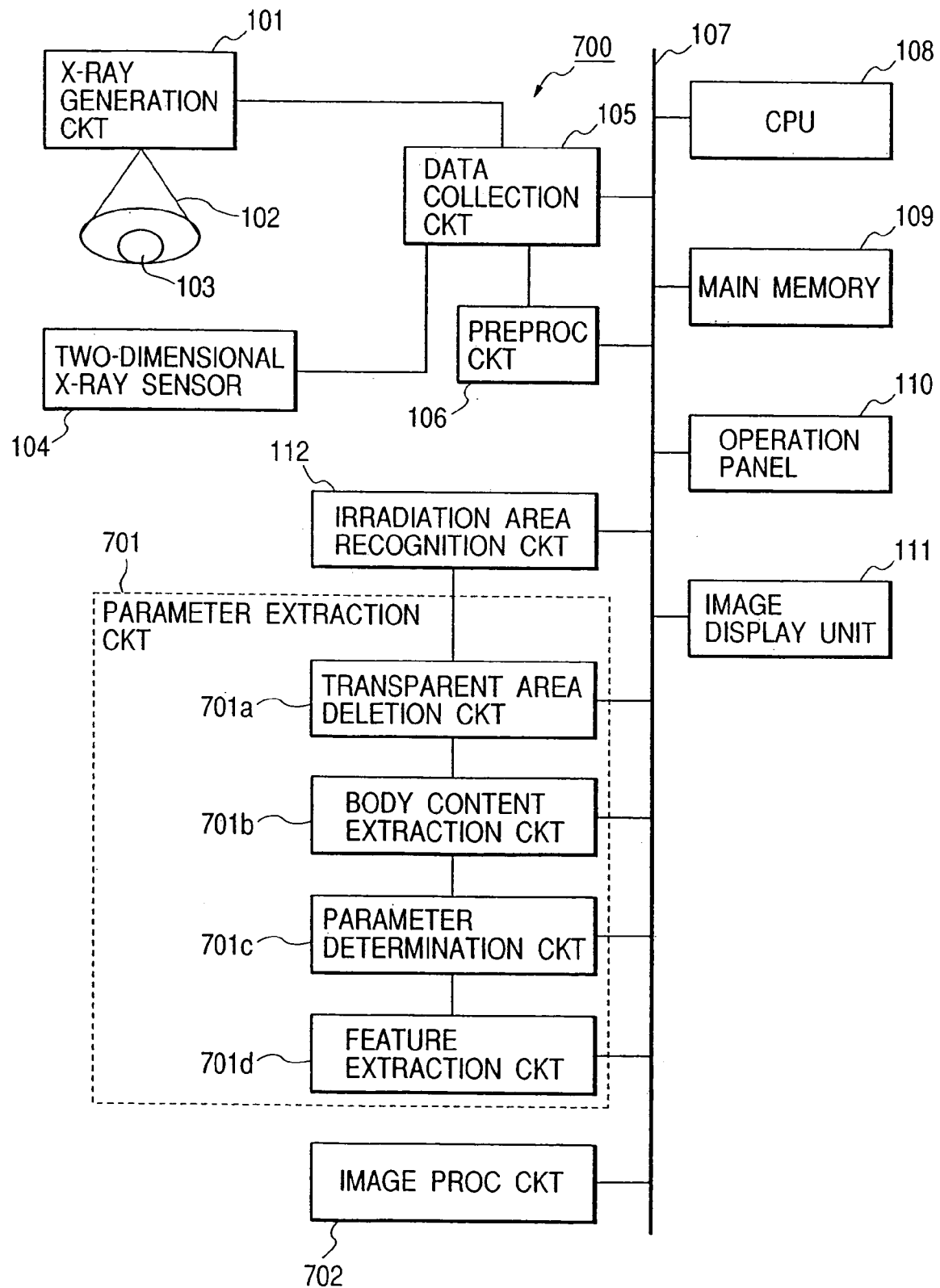
FIG. 10 is a block diagram showing a structure of an X-ray photographing apparatus according to the third embodiment of the present invention.

The present embodiment is applied to, e.g., such an X-ray photographing apparatus 700 as shown in FIG. 10.

The X-ray photographing apparatus 700 has an image processing function for a photographed image. As shown in FIG. 10, the X-ray photographing apparatus 700 includes an X-ray generation circuit 101 which generates an X-ray beam 102, a two-dimensional X-ray sensor 104 on which the X-ray beam 102 penetrated through a subject 103 is imaged, a data collection circuit 105 which collects photographed images output from the two-dimensional X-ray sensor 104, a preprocessing circuit 106 which performs preprocessing to the photographed images collected by the data collection circuit 105, a main memory 109 which stores various information such as the photographed image (original image) subjected to the preprocessing by the preprocessing circuit 106 and processing programs to perform various processing, an operation panel 110 which is used to instruct X-ray photographing and perform various setting to the X-ray photographing apparatus 700, an irradiation area recognition circuit 112 which extracts an irradiation area from the photographed image (original image) subjected to the preprocessing by the preprocessing circuit 106, a parameter extraction circuit 701 which extracts parameters used for various image processing including the irradiation area image obtained by the irradiation area recognition circuit 112, an image processing circuit 702 which performs image processing such as the gradation conversion processing or the like to the photographed image (original image) subjected to the preprocessing by using information obtained by the parameter extraction circuit 701, an image display unit 111 which displays the photographed image subjected to the image processing by the image processing circuit 702, and a CPU 108 which controls an operation of the X-ray photographing apparatus 700 as a whole. The data collection circuit 105, the preprocessing circuit 106, the irradiation area recognition circuit 112, the parameter extraction circuit 701, the image processing circuit 702, the CPU 108, the main memory 109, the operation panel 110 and the image display unit 111 are all connected to a CPU bus 107 such that data can be transferred and received among these units.

The parameter extraction circuit 701 which is structured to change the parameter used for the image processing of the image processing circuit 702 in accordance with a state of a subject (e.g., a constitution of the subject) on the photographed image is the most important feature in the present embodiment.

Thus, the parameter extraction circuit 701 includes a transparent area deletion circuit 701a, a body area content extraction circuit 701b, a parameter determination circuit 701c, and a feature extraction circuit 701d. The transparent area deletion circuit 701a performs semibinarization processing which replaces pixels in an area outside the irradiation area extracted by the irradiation area recognition circuit 112, pixels in an area having a pixel value equal to or larger than a certain threshold, and pixels in an area within a certain range of these areas, by "0". The body area content extraction circuit 701b calculates content or space (i.e., a body area content or space) of a pixel area having a pixel value other than "0", from the image processed by the transparent area deletion circuit 701a. The parameter determination circuit 701c determines the various image processing parameters used by the image processing circuit 702, from the body area content calculated by the body area content extraction circuit 701b. On the basis of the parameters determined by the parameter determination circuit 701c, the feature extraction circuit 701d extracts the maximum value from the pixel area having the pixel value other than "0" in the image again processed by the transparent area deletion circuit 701a.

Therefore, the image processing circuit 702 uses, e.g., the maximum value extracted by the feature extraction circuit 701d, as the feature quantity. Besides, the image processing circuit 702 performs gradation conversion processing to the photographed image by using the parameter (e.g., a gradation conversion curve) determined by the parameter determination circuit 701c.

Figure 11:
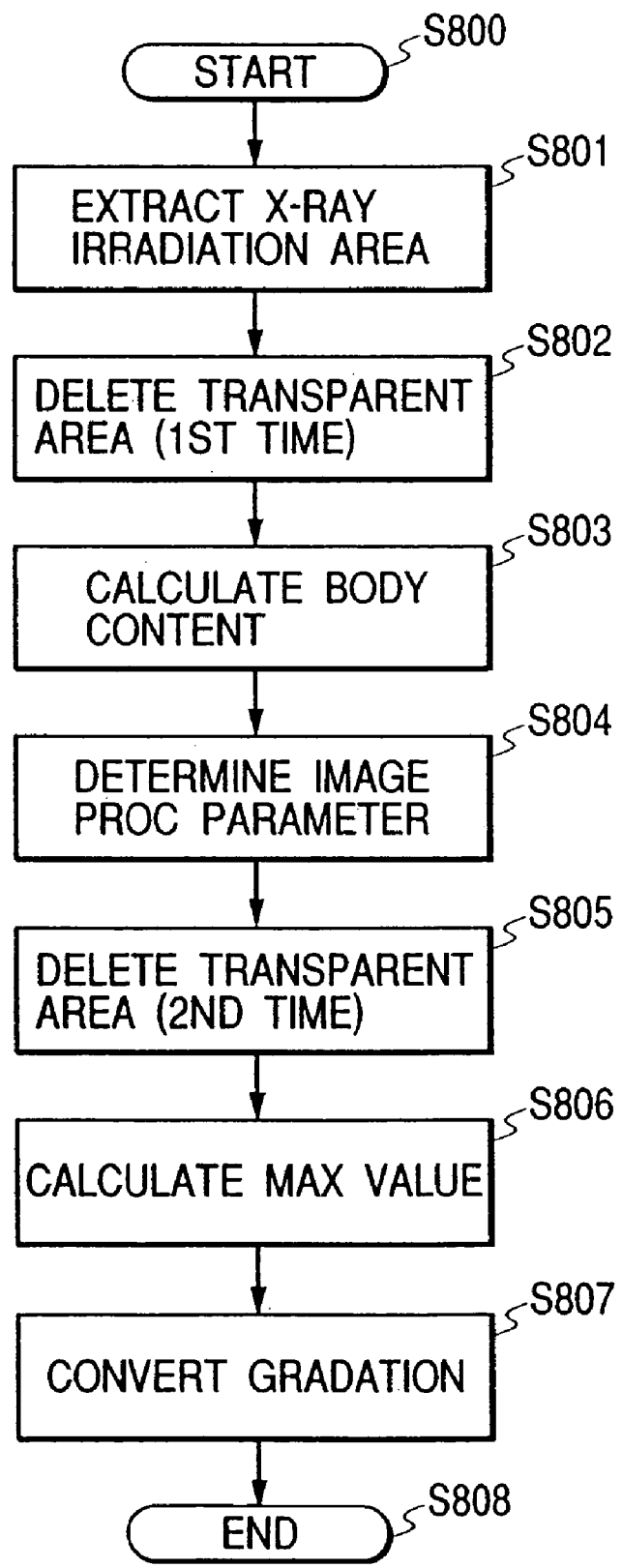
FIG. 11 is a flow chart for explaining an operation of the X-ray photographing apparatus.
Figure 12:
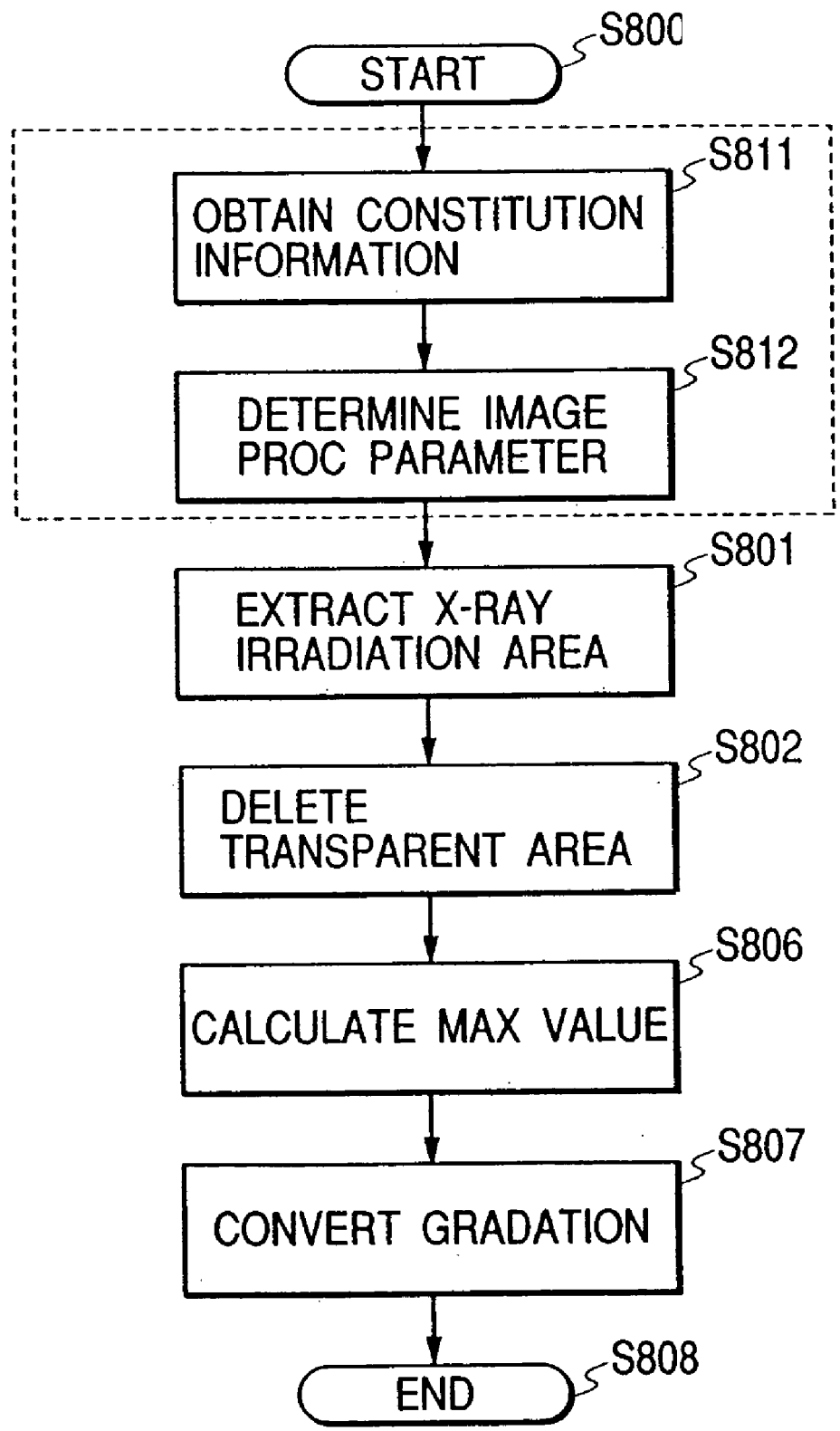
FIG. 12 is a flow chart for explaining an operation of an X-ray photographing apparatus according to the fourth embodiment of the present invention.

In such the X-ray photographing apparatus 700 as above, initially data which is necessary for performing various processing by the CPU 108, processing programs and the like are previously stored in the main memory 109. Besides, the main memory 109 includes a working memory for the CPU 108. As the processing program which is previously stored in the main memory 109, for example, processing programs according to flow charts shown in FIGS. 11 and 12 are used.

Therefore, the CPU 108 reads the processing programs from the main memory 109 and executes the read programs, thereby controlling the entire operation of the X-ray photographing apparatus 700 according to instructions from the operation panel 110, as explained below.

In the X-ray photographing apparatus 700 of FIG. 10, the parts which function as well as the parts in the X-ray photographing apparatus 100 of FIG. 1 are added with the same reference numerals as those in FIG. 1 respectively, and detailed explanation thereof will be omitted.

In a step S800, the X-ray generation circuit 101 generates the X-ray beam 102 to the subject (i.e., a body to be examined) 103. The X-ray beam 102 generated by the X-ray generation circuit 101 penetrates the subject 103 while attenuating, and reaches the two-dimensional X-ray sensor 104. Then the X-ray beam 102 is output as an X-ray image by the X-ray sensor 104. In the present embodiment, it is assumed that the X-ray image output from the X-ray sensor 104 is a human body image.

Next, the data collection circuit 105 converts the X-ray image output from the two-dimensional X-ray sensor 104 into an electrical signal, and supplies the obtained signal to the preprocessing circuit 106.

The preprocessing circuit 106 performs the preprocessing such as offset correction processing, gain correction processing and the like to the signal (X-ray image signal) supplied from the data collection circuit 105. Under the control of the CPU 108, the X-ray image signal subjected to the preprocessing by the preprocessing circuit 106 is transferred as input image information to the main memory 109, the irradiation area recognition circuit 112, the parameter extraction circuit 701 and the image processing circuit 702, through the CPU bus 107.

In a step S801, the irradiation area recognition circuit 112 extracts an X-ray irradiation area from an input image (also called a target image hereinafter) transferred under the control of the CPU 108, with use of an arbitrary method.

On the basis of the irradiation area extracted by the irradiation area recognition circuit 112, the parameter extraction circuit 701 performs processing in later-described steps S802, S803, S804, S805 and S806. Thus, the circuit 701 extracts, from the input image transferred under the control of the CPU 108, the image processing parameters used by the image processing circuit 702.

First, in the step S802, the transparent area deletion circuit 701a replaces, in the input image, pixels of a transparent area within the irradiation area and pixels of an area adjacent to the transparent area in a certain interval by, e.g., the pixel value="0".

Concretely, the image is converted as input image data f(x, y) by using a following expression (11), thereby obtaining image data f1 (x, y) after the processing.

$$f1(x, y) = f(x, y) \times \prod_{x1=-d1}^{x1=d1} \prod_{y1=-d2}^{y1=d2} \text{sgn}(x + x1, y + y1) \quad (11)$$

Here, sgn(x, y) in the expression (11) is represented by using an expression (12).

sgn(x, y)=0 when f(x, y)>Th1 sgn(x, y)=1 when other cases (12)

In the expression (12), the constant Th1 is previously obtained by an experiment or the like. For example, it is assumed that the constant Th1 is 5% of the maximum value of the pixel value of the entire input image. Further, the constants d1 and d2 in the expression (11) are used to determine the certain interval (certain width) of the body adjacent to the transparent area. It is assumed that, in first transparent area deletion, d1=0 and d2=0 are set.

In the transparent area deletion circuit 701a of the present embodiment, the pixel value is replaced by "0". However, the pixel value may be replaced by an arbitrary certain numeral other than "0" or "1".

Next, in the step S803, the body area content extraction circuit 701b calculates, in the image f1 (x, y) obtained by the transparent area deletion circuit 701a, a content (body area content) s1 of the pixel area having the value other than "0", by using following expressions (13) and (14).

sgn1(x)=0 when x=0 sgn1(x)=1 when other cases (13)

s1=∫∫sgn1(f1(x, y))dxdy (14)

In the step S804, the parameter determination circuit 701c determines the parameters d1 and d2 used in second processing by the transparent area deletion circuit 701a and the parameter used in the image processing by the image processing circuit 702 (i.e., an inclination γ of the gradation conversion curve used in the gradation conversion processing in this case), in accordance with the body area content s1 obtained by the body area content extraction circuit 701b.

For example, in a case where the input image f(x, y) includes 168×168 pixels, d1=d=20, γ=2.5 when 10000≦s1,
d1=d2=17, γ=2.883 when 8000≦s1<10000,
d1=d2=14, γ=3.2 when 4000≦s1≦8000, and
d1=d2=8, γ=3.8 when s1≦4000.

Thus, the various parameters are determined according to the body area content s1.

In the step S805, the transparent area deletion circuit 701a performs processing based on the above expression (12) and a following expression (15), by using the parameters d1 and d2 determined by the parameter determination circuit 701c, thereby obtaining image data f2 (x, y) after second processing.

$$f2(x, y) = f(x, y) \times \prod_{x1=-d1}^{x1=d1} \prod_{y1=-d2}^{y1=d2} \text{sgn}(x + x1, y + y1) \quad (15)$$

In a step S806, the feature extraction circuit 701d extracts the maximum pixel value from the image data f2 (x, y) obtained in the second processing of the transparent area deletion circuit 701a.

In a step S807, when the image processing circuit 702 performs, e.g., gradation conversion processing to an input image transferred under the control of the CPU 108, the circuit 702 uses as the feature quantity the maximum value obtained by the feature extraction circuit 701d. Besides, the image processing circuit 702 performs the image gradation conversion such that the feature quantity has certain density (e.g., 1.9), by using the gradation conversion curve of the inclination γ determined by the parameter determination circuit 701c.

In a step S808, the image which was subjected to the image processing such as the gradation conversion or the like by the image processing circuit 702 is displayed on the image display unit 111 or output on a film.

As described above, in the present embodiment, the parameter used in the image processing is changed according to the state of the subject (the content of the body area in this case) on the photographed image, whereby it is possible to perform the optimum image processing according to the photographed image.

Further, the content of the body area is extracted by deleting the transparent area and the area outside the irradiation area, and the image processing parameter is determined according to the extracted body area content. Thus, even if the transparent area changes due to the size (e.g., the constitution) of the subject on the photographed image, it is possible to accurately determine the image processing parameter to the photographed image.

Further, as the body area content grows, the density distribution tends to extend. In the present embodiment, the inclination of the gradation conversion curve is changed according to the body area content, whereby it is possible to perform the gradation conversion suitable for the photographed image. Especially, in the present embodiment, almost the maximum value is extracted as the feature quantity in the image obtained by photographing a lung, and the gradation conversion is performed by using the extracted feature quantity. Thus, it is possible to stably obtain the image suitable for diagnosis.

(Fourth Embodiment)

In the present embodiment, the operation of the X-ray photographing apparatus 700 in the above third embodiment is replaced by an operation according to a flow chart shown in FIG. 12.

It should be noted that, in the flow chart of FIG. 12, the same processing steps as those in the flow chart of FIG. 11 are respectively added with the same reference numerals, and detailed explanation thereof will be omitted. In the present embodiment, only processing (see the part enclosed with the dotted line in FIG. 12) which is different from the third embodiment will be explained concretely.

First, in a step S811, a parameter determination circuit 701c obtains subject information on, e.g., stature, weight, shoulder breadth, chest, hips and the like of a subject on a photographed image, from an operation panel 110 or the like.

Next, in a step S812, the parameter determination circuit 701c determines the parameter corresponding to the subject information obtained in the step S811, from a table in which plural image processing parameters have been previously registered. At this time, the circuit 701c selects and determines the optimum parameter in accordance with a combination of a part of various information included in the subject information or all the information.

According to the present embodiment described as above, it is unnecessary to calculate the body area content information of the subject from the photographed image. Thus, it is possible to easily determine the image processing parameter and thus shorten the processing time. Besides, it is possible to perform the optimum image processing according to the state of the subject to be photographed.

It is needless to say that the object of the present invention can be achieved also in a case where a storage medium storing the program codes of software for realizing the functions of the above-described embodiments is supplied to a system or an apparatus and then a computer (or CPU or MPU) in the system or the apparatus reads and executes the program codes stored in the memory medium.

In this case, the program codes themselves read from the storage medium realize the function of each embodiment, and the storage medium storing such the program codes constitutes the present invention.

The storage medium storing the program codes can be, e.g., a ROM, a floppy disk, a hard disk, an optical disk, a magnetooptical disk, a CD-ROM, a CD-R, a magnetic tape, a non-volatile memory card, or the like.

It is needless to say that the present invention also includes not only the case where the functions of the embodiments are realized by executing the program codes read by the computer, but also a case where an OS (operating system) or the like functioning on the computer executes all the process or a part thereof according to instructions of the program codes, thereby realizing the functions of the embodiments.

Further, it is needless to say that the present invention further includes a case where the program codes read from the storage medium are once stored in a memory provided in a function expansion board inserted in the computer or a function expansion unit connected to the computer, and a CPU or the like provided in the function expansion board or the function expansion unit executes all the process or a part thereof according to instructions of the program codes, thereby realizing the functions of the embodiments.

Although the present invention has been explained by using the preferred embodiments, the present invention is not limited to the structures of these embodiments. That is, it is needless to say that various modifications and changes are possible in the present invention without departing from the spirit and scope of the appended claims.

What is claimed is:

1. An image processing apparatus for processing an image of an object, comprising:
    an extracting unit adapted to extract from the processed image a first area wherein a sensor detects an X-ray which does not pass through the object, and an area of a certain width which is in contact with the first area, wherein said area of a certain width is included in a second area where the sensor detects an X-ray passing through the object in an image output from the sensor; and
    an image processing unit adapted to process the image except for a part of the image in the first area and said area of a certain width which is in contact with the first area.

2. An image processing apparatus according to claim 1, wherein said extracting unit extracts said area of a certain width which is in contact with the first area by extracting a pixel within a certain distance from a pixel in the first area.

3. An image processing apparatus according to claim 1,
    wherein said image processing unit has a calculating circuit for calculating a feature quantity based on the image except for a part of the image in the first area and said area of a certain width which is in contact with the first area, and said image processing apparatus further comprises a gradation conversion unit adapted to perform gradation conversion of the image using a gradation conversion curve based on the feature quantity.

4. An image processing apparatus according to claim 3, further comprising a calculating unit adapted to calculate a superficial content of an area of the object.

5. An image processing apparatus according to claim 1, further comprising:
    an X-ray generation circuit for radiating X-rays;
    a two-dimensional X-ray sensor for obtaining, as the image, the X-rays penetrating the objects,
    wherein the sensor is a two-dimensional X-ray sensor.

6. An image processing method for processing an image of an object, comprising:
    an extracting step of extracting from the processed image a first area wherein a sensor detects an X-ray which does not pass through the object, and an area of a certain width which is in contact with the first area, wherein said area of a certain width is included in a second area where the sensor detects an X-ray passing through the object in an image output from the sensor; and
    an image processing step of processing the image except for a part of the image in the first area and said area of a certain width which is in contact with the first area.

7. A computer-readable storage medium which stores a program to achieve an image processing method for processing an image of an object, comprising:
    an extracting step of extracting from the processed image a first area wherein a sensor detects an X-ray which does not pass through the object, and an area of a certain width which is in contact with the first area, wherein said area of a certain width is included in a second area where the sensor detects an X-ray passing through the object in an image output from the sensor; and
    an image processing step of processing the image except for a part of the image in the first area and said area of a certain width which is in contact with the first area.

8. An image processing method according to claim 6, wherein said extracting step extracts said area of a certain width which is in contact with the first area by extracting a pixel within a certain distance from a pixel in the first area.

9. A computer-readable storage medium according to claim 7, wherein said extracting step extracts said area of a certain width which is in contact with the first area by extracting a pixel within a certain distance from a pixel in the first area.

* * * * *

UNITED STATES PATENT AND TRADEMARK OFFICE
CERTIFICATE OF CORRECTION

PATENT NO. : 7,139,419 B2
APPLICATION NO. : 10/857855
DATED : November 21, 2006
INVENTOR(S) : Hiroyuki Shinbata It is certified that error appears in the above-identified patent and that said Letters Patent is hereby corrected as shown below:

COLUMN 1

Line 56, "such the" should read --such a--.
Line 59, "such the" should read --such an--.

COLUMN 2

Line 25, "such the" should read --such an--.
Line 44, "an" should read --a--.

COLUMN 4

Line 4, "what one" should read --that one--.
Line 21, "such the" should read --such an--.

COLUMN 5

Line 34, "f(x, y)>Th1sgn(x, y)=1" should read
--f(x, y) $\geq$ Th1
sgn(x, y)=1--.

COLUMN 6

Line 3, "Y1<y$\leq$Y2," should read --Y1$\leq$y$\leq$Y2,--.
Line 36, "such the" should read --such a--.
Line 37, "what" should read --that--
Line 38, "such the" should read --such a--.
Line 48, "such the" should read --such a--.

COLUMN 7

Line 23, "f1(x, y)$\leq$Th2sgn(x, y)=0" should read
--f1(x, y)$\geq$Th2
sgn(x, y)=0--.

COLUMN 8

Line 4, "such the" should read --such a--.

UNITED STATES PATENT AND TRADEMARK OFFICE
CERTIFICATE OF CORRECTION

PATENT NO.         : 7,139,419 B2
APPLICATION NO.    : 10/857855
DATED              : November 21, 2006
INVENTOR(S)        : Hiroyuki Shinbata It is certified that error appears in the above-identified patent and that said Letters Patent is hereby corrected as shown below:

COLUMN 9

Line 7, "such the" should read --such an--.

COLUMN 10

Line 31, "$f(x, y) \geqq Th\ sgn(x, y)=1$" should read
        --$f(x, y) \geqq Th$
          $sgn(x, y)=1$--.
    Line 38, "then" should read --than--.
    Line 56, "Such the" should read --Such an--.

COLUMN 12

Line 36, "such the" should read --such an--.

COLUMN 13

Line 34, "$f(x, y)>Th1 sgn(x, y)=1$" should read
        --$f(x, y) \geq Th1$
          $sgn(x, y)=1$--.
    Line 58, "$x=0 sgn1(x)=1$" should read
        --$x=0$
          $sgn1(x)=1$--.

COLUMN 15

Line 40, "such the" should read --such--.

UNITED STATES PATENT AND TRADEMARK OFFICE
CERTIFICATE OF CORRECTION

| | |
|---|---|
| PATENT NO. | : 7,139,419 B2 |
| APPLICATION NO. | : 10/857855 |
| DATED | : November 21, 2006 |
| INVENTOR(S) | : Hiroyuki Shinbata |

It is certified that error appears in the above-identified patent and that said Letters Patent is hereby corrected as shown below:

<u>COLUMN 16</u>

Line 37, "objects,' should read --object,--.

Signed and Sealed this

Thirtieth Day of October, 2007

JON W. DUDAS
*Director of the United States Patent and Trademark Office*